United States Patent
Wilkinson

(10) Patent No.: US 7,150,725 B2
(45) Date of Patent: Dec. 19, 2006

(54) PASSIVE ACTIVATED SAFETY BLOOD COLLECTION SET

(75) Inventor: Bradley Wilkinson, North Haledon, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 152 days.

(21) Appl. No.: 10/738,872

(22) Filed: Dec. 17, 2003

(65) Prior Publication Data

US 2005/0137528 A1 Jun. 23, 2005

(51) Int. Cl.
*A61M 5/32* (2006.01)
*A61M 5/00* (2006.01)

(52) U.S. Cl. .................. 604/162; 604/171; 604/198

(58) Field of Classification Search .............. 604/110, 604/198, 263, 162, 163, 164.01, 164.07, 604/164.08, 164.09, 165.03, 171, 174, 177, 604/179, 187, 192
See application file for complete search history.

(56) References Cited

U.S. PATENT DOCUMENTS

| | | | |
|---|---|---|---|
| 3,840,008 A | 10/1974 | Noiles | |
| 4,139,009 A | 2/1979 | Alvarez | |
| 4,725,267 A | 2/1988 | Vaillancourt | |
| 4,735,618 A | 4/1988 | Hagen | |
| 4,867,746 A | 9/1989 | Dufresne | |
| 4,892,521 A | 1/1990 | Laico et al. | |
| 4,909,794 A | 3/1990 | Haber et al. | |
| 4,998,922 A | 3/1991 | Kuracina et al. | |
| 5,098,401 A | 3/1992 | De Lange | |
| 5,176,655 A | 1/1993 | McCormick et al. | |
| 5,242,418 A | 9/1993 | Weinstein | |
| 5,250,031 A | 10/1993 | Kaplan et al. | |
| 5,256,152 A | 10/1993 | Marks | |
| 5,295,972 A | 3/1994 | Mischenko | |
| 5,348,544 A | 9/1994 | Sweeney et al. | |
| 5,423,766 A | 6/1995 | Di Cesare | |
| 5,538,508 A | 7/1996 | Steyn | |
| 5,779,679 A | 7/1998 | Shaw | |
| 6,210,371 B1 | 4/2001 | Shaw | |
| D452,003 S | 12/2001 | Niermann | |
| D452,313 S | 12/2001 | Niermann | |

(Continued)

FOREIGN PATENT DOCUMENTS

| | | |
|---|---|---|
| EP | 1 254 677 A1 | 11/2002 |
| EP | 1 346 738 A1 | 9/2003 |
| EP | 1 369 142 A1 | 12/2003 |
| EP | 1 374 772 A1 | 1/2004 |

*Primary Examiner*—Kevin C. Sirmons
*Assistant Examiner*—Mark K Han
(74) *Attorney, Agent, or Firm*—Mark J. Schildkraut

(57) ABSTRACT

A shieldable needle device including a needle cannula, a hub, a pair of wings extending laterally from opposing sides of the hub, a tip guard axially movable along the needle cannula from a proximal position substantially adjacent the hub to a distal position, and a drive member is disclosed. The drive member includes a first end connected to the hub and a second end connected to the tip guard and is extendable between a folded biased position and an extended position for moving the tip guard from the proximal position to the distal position. The pair of wings, when in a dorsal position, retain the drive member in the folded biased position maintaining the tip guard in a proximal position. Upon release of the wings, the drive member unfolds, extending the tip guard from the proximal position toward the distal position.

14 Claims, 7 Drawing Sheets

U.S. PATENT DOCUMENTS

| | | |
|---|---|---|
| D452,314 S | 12/2001 | Niermann |
| 6,537,259 B1 | 3/2003 | Niermann |
| 6,682,510 B1 | 1/2004 | Niermann |
| 6,918,891 B1 * | 7/2005 | Bressler et al. ............. 604/198 |
| 2002/0111566 A1 | 8/2002 | Maclean |
| 2003/0036731 A1 | 2/2003 | Wilkinson et al. |
| 2003/0135157 A1 | 7/2003 | Saulenas et al. |
| 2003/0181870 A1 * | 9/2003 | Bressler et al. ............. 604/263 |

* cited by examiner

PASSIVE ACTIVATED SAFETY BLOOD COLLECTION SET

BACKGROUND OF THE INVENTION

1. Field of the Invention

The present invention relates to blood collection sets for safe and convenient handling of needles. More particularly, the present invention relates to a low cost disposable blood collection set including a needle assembly having a safety shield.

2. Description of Related Art

Disposable medical devices having piercing elements are typically used for administering a medication or withdrawing a fluid, such as blood collecting needles, fluid handling needles and assemblies thereof. Current medical practice requires that the fluid containers and needle assemblies used in such systems be inexpensive and readily disposable. Consequently, existing blood collection systems, for example, typically employ some form of durable, reusable holder on which detachable and disposable needles and fluid collection tubes may be mounted. A blood collection system of this nature can be assembled prior to use and then disassembled after usage. Thus, these blood collection systems allow repeated use of the relatively expensive holder upon replacement of the relatively inexpensive needle and/or fluid collection tube. In addition to reducing the cost of collecting blood specimens, these blood collection systems also help minimize the production of hazardous medical waste.

A blood collection set or intravenous (IV) infusion set typically includes a needle cannula having a proximal end, a pointed distal end and a lumen extending therebetween. The proximal end of the needle cannula is securely mounted in a plastic hub with a central passage that communicates with the lumen through the needle cannula. A thin flexible thermoplastic tube is connected to the hub and communicates with the lumen of the needle cannula. The end of the plastic tube remote from the needle cannula may include a fixture for connecting the needle cannula to a blood collection tube or some other receptacle. The specific construction of the fixture will depend upon the characteristics of the receptacle to which the fixture will be connected.

In order to reduce the risk of incurring an accidental needle-stick wound, protection of used needle tips becomes important. With concern about infection and transmission of diseases, methods and devices to enclose the used disposable needle have become very important and in great demand. For example, needle assemblies commonly employ a safety shield that can be moved into shielding engagement with a used needle cannula without risking an accidental needle stick.

Some needle shields are referred to as tip guards, and include a small rigid guard that can be telescoped along the length of a needle cannula and extended over the puncture tip of the needle for protection. Such conventional tip guards may include some form of tether for limiting the travel of the tip guard to the length of the needle cannula. Additionally, such conventional tip guards typically include a structure that lockingly engages over the tip of the used needle cannula to prevent a re-exposure of the needle. The structure for preventing re-exposure may include a metallic spring clip or a transverse wall integrally formed with one end of the tip guard. Needle assemblies including such tip guards, however, typically include extensive mechanics for positioning of the tip guard, resulting in complex arrangements which are costly to manufacture and assemble. Also, operation of the tip guard can involve substantial manipulation by the user to extend the tip guard to a shielding position.

U.S. patent Publication No. 2002/0099339 discloses a safety shield for needles which includes a pair of deflectable leaves on opposing lateral sides of a needle assembly for moving a tip guard along the needle to a shielding position. In use, the deflectable leaves are released causing the leaves to extend or unfold to move the tip guard along the needle to the shielding position.

While prior art devices provide for effective shielding of used needles, a need remains for needle assemblies for use with a blood collection set which achieve secure and effective shielding of a used needle tip while maintaining a low profile and providing a defined gripping structure to aid in positioning of the needle for insertion, and which is simple and inexpensive to manufacture and easy to operate.

SUMMARY OF THE INVENTION

The present invention is directed to a shieldable needle device, particularly useful in connection with a blood collection set. The needle device includes a needle cannula having opposed proximal and distal ends and a hub supporting a proximal end of the needle cannula. The proximal end of the hub may be adapted for mating with a medical device, whereby a flexible tube, including a structure for mating with a blood collection assembly, may extend from the proximal end of the hub. The needle device further includes a pair of bendable wings having surfaces extending laterally from opposing sides of the hub, a tip guard, and a drive member.

The tip guard is axially movable along the needle cannula from a proximal position substantially adjacent the hub to a distal position where the tip guard protectively surrounds the distal end of the needle cannula.

The drive member includes a first flexible member connected between the hub and the tip guard, and extends between a folded biased position and an extended position for moving the tip guard from the proximal position to the distal position. The pair of wings are bendable between a laterally extending position and a dorsal position and may also be integrally formed with a hub. When in a dorsal position, the pair of wings retain the drive member in the folded bias position, to maintain the tip guard in the proximal position. When the pair of wings are in a dorsal position, a gap may also be created between the hub and the wing surfaces, whereby a portion of the drive member in the folded biased position is retained internal to the gap. Upon release of the wings from the dorsal position to the laterally extending position, the created gap is eliminated and the drive member is permitted to unfold and extend the tip guard from the proximal position toward the distal position.

The tip guard may include a tip guard housing formed from a plastic material with a metallic spring clip mounted to the housing. The spring clip is biased against the needle cannula when the tip guard is in the proximal position and is being resiliently moved over the distal end of the needle cannula when the tip guard is in the distal position. The shieldable needle device may also include a packaging cover having an opening for protectively surrounding the needle cannula. The packaging cover may include structure for removably mating with the device and may include a slot area for maintaining the wings in the dorsal position.

In another embodiment, the present invention is directed to a method for shielding a medical needle device. The method includes providing a shieldable needle device as described hereinabove, providing a removable packaging cover, and removing the packaging cover from the shieldable needle device. The packaging cover protectively surrounds the needle cannula and maintains the pair of wings in the dorsal position to allow the pair of wings to retain the drive member in the folded bias position between the wings. The packaging cover is removed from the shieldable needle device, thereby releasing the wings from the dorsal position to the laterally extending position and allowing the drive member to unfold and extend the tip guard from the proximal position toward the distal position.

DETAILED DESCRIPTION

Figure 1:
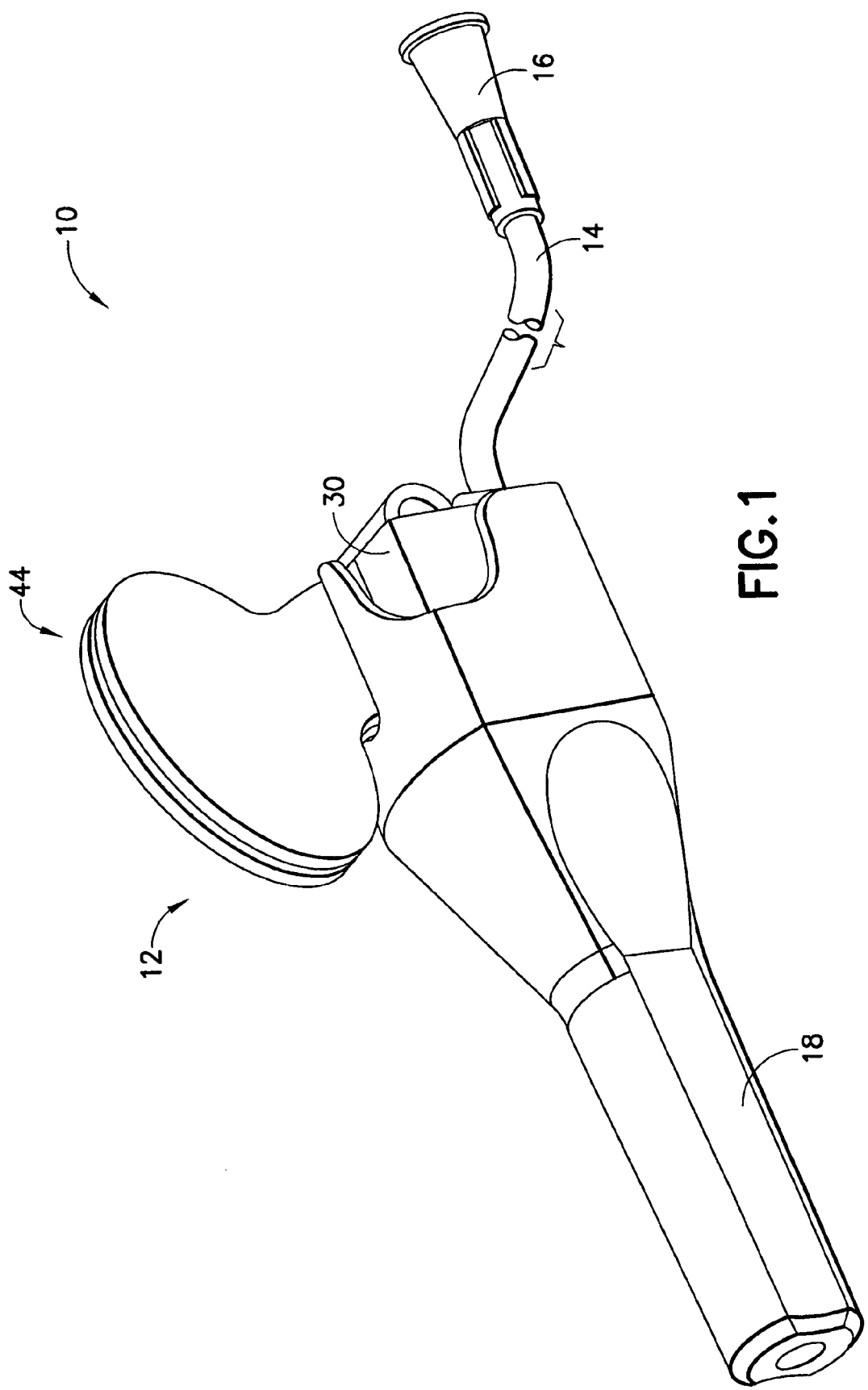
FIG. 1 is a perspective view of a shieldable needle device in accordance with the present invention including a packaging cover thereon.
Figure 2:
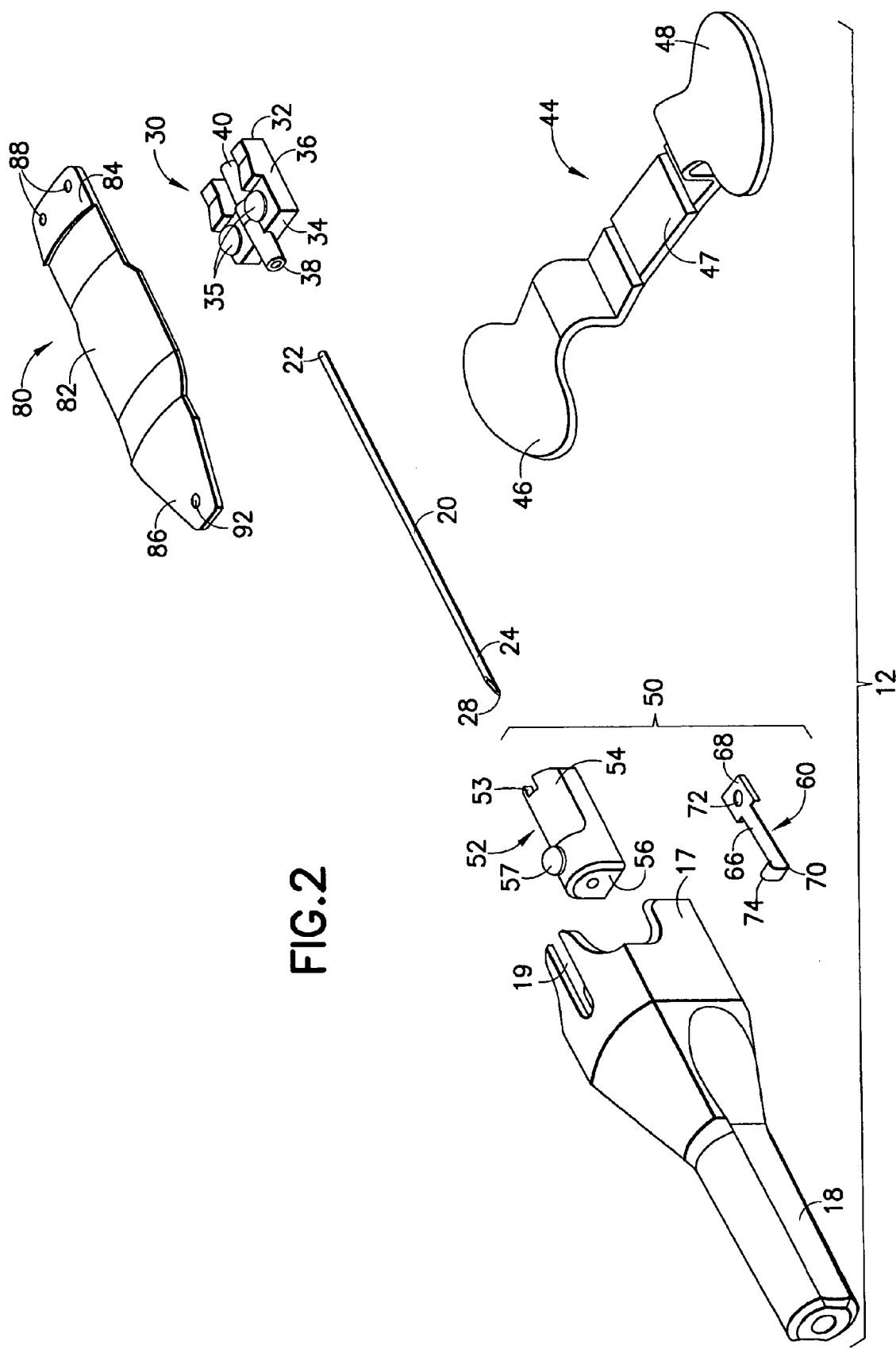
FIG. 2 is an exploded perspective view of the shieldable needle device of the present invention.

Referring to the drawings in which like reference characters refer to like parts throughout the several views thereof, FIG. 1 illustrates a blood collection set in accordance with the present invention and the related features. The present invention is generally described in terms of a blood collection set, and encompasses such a blood collection set, as well as a shieldable needle assembly for use in such a blood collection set.

As shown in FIG. 1, blood collection set 10 includes a shieldable needle device 12, a flexible tube 14 extending from needle device 12, a fixture 16 mounted to tube 14, and a packaging cover 18 removably mounted to portions of needle device 12 opposite tube 14, such as through a frictional engagement. Shieldable needle device 12 of blood collection set 10 is shown in detail in FIGS. 2–7, and generally includes a needle cannula 20, a hub 30, a tip guard assembly 50 and a drive member 80 for moving the tip guard assembly 50.

Needle cannula 20 includes a proximal end 22 and an opposing distal end 24, with lumen 26 extending through needle cannula 20 from proximal end 22 to distal end 24. Distal end 24 of needle cannula 20 is beveled to define a sharp puncture tip 28, such as an intravenous puncture tip. Puncture tip 28 is provided for insertion into a patient's blood vessel, such as a vein, and is therefore designed to provide ease of insertion and minimal discomfort during venipuncture.

Needle assembly 12 further includes hub 30. Hub 30 is a unitary structure, desirably molded from a thermoplastic material. Hub 30 includes a proximal end 32, a distal end 34, and is defined by a rigid structure 36 extending between the ends. The distal end 34 of hub 30 includes structure for mating with drive member 80, such as two button elements 35 for connection with the drive member 80, as will be discussed in more detail hereinafter. Structure 36 having an underside 37 includes an opening 38 at the distal end of the structure 36 for receiving the proximal end 22 of the needle cannula 20. Needle cannula 20 is positioned within opening 38 of hub 30, and extends from distal end 34 of hub 30. Desirably, needle cannula 20 and hub 30 are separate parts which are fixedly attached and secured through an appropriate medical grade adhesive, for example, epoxy or the like. Additionally, an opening 40 at the proximal end of the structure 36 is adaptable to receive flexible tube 14, or other medical device, such as a tube holder, or the like.

Figure 4:
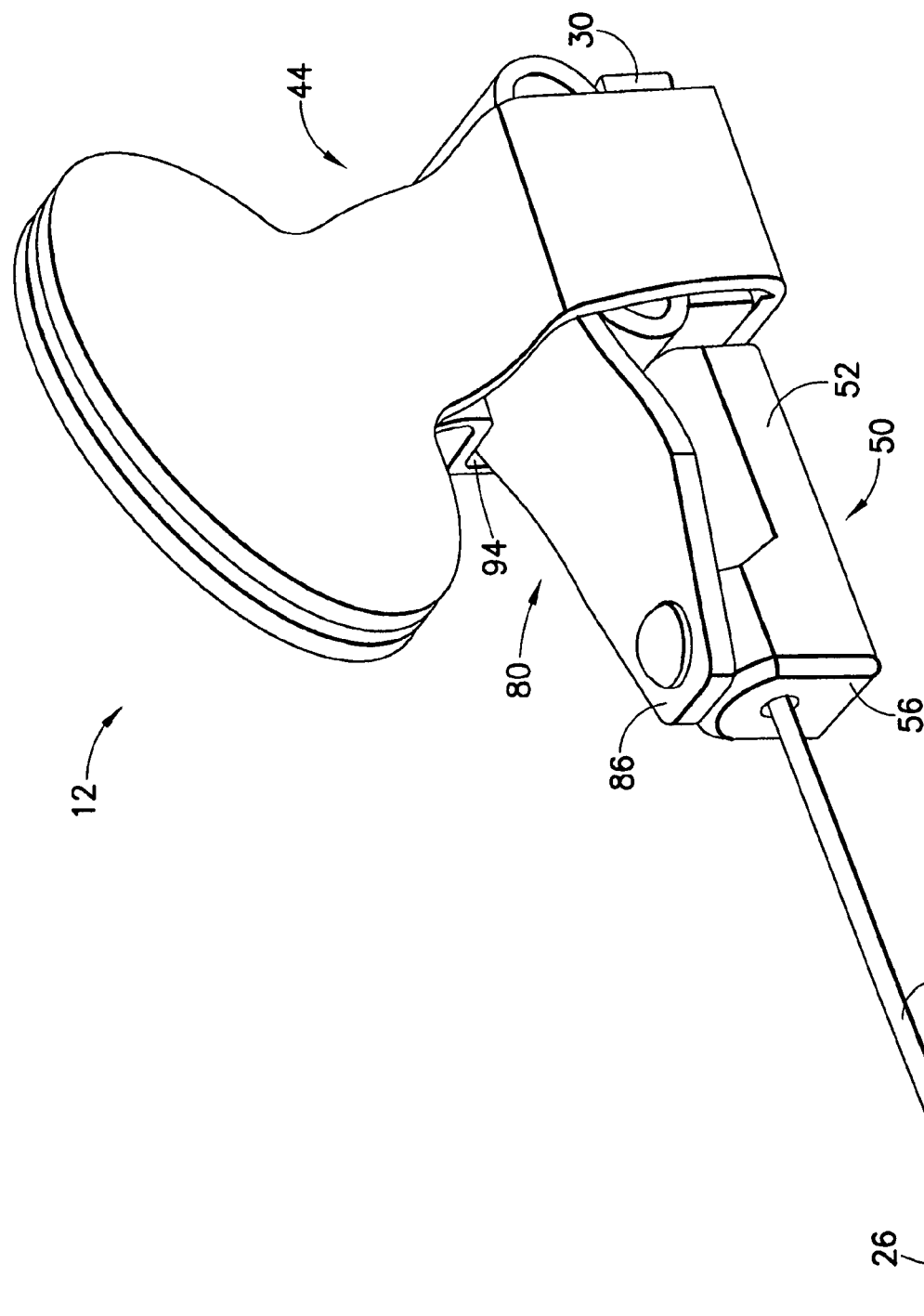
FIG. 4 is a perspective view of the shieldable needle device of FIG. 1 with the packaging cover removed.

Hub 30 further includes a wing element 44 including a body 47 extending between a pair of wings 46 and 48. Body 47 of wing element 44 may be fixedly attached to the underside 37 of the hub, thereby allowing wings 46 and 48 to extend laterally from structure 36 at opposing sides thereof. Wings 46 and 48 provide hub 30, and needle assembly 12, as a butterfly-type wing assembly, assistance in positioning, stabilizing and placement of needle assembly 12 and blood collection set 10 during a blood collection procedure. Wings 46 and 48 are preferably of a flexible material, and are bendable between a relaxed, laterally extending position in which they are substantially planar, to a bent dorsal position, as shown in FIG. 4. While wings 46 and 48 may be a preformed bent structure, wings 46 and 48 may also be a planar structure, for example wing surfaces having a skive portion to assist in folding wings 46 and 48 to a dorsal position. Wings 46 and 48 may further be a co-molded part with hub 30, exhibiting soft and rigid properties.

Figure 5:
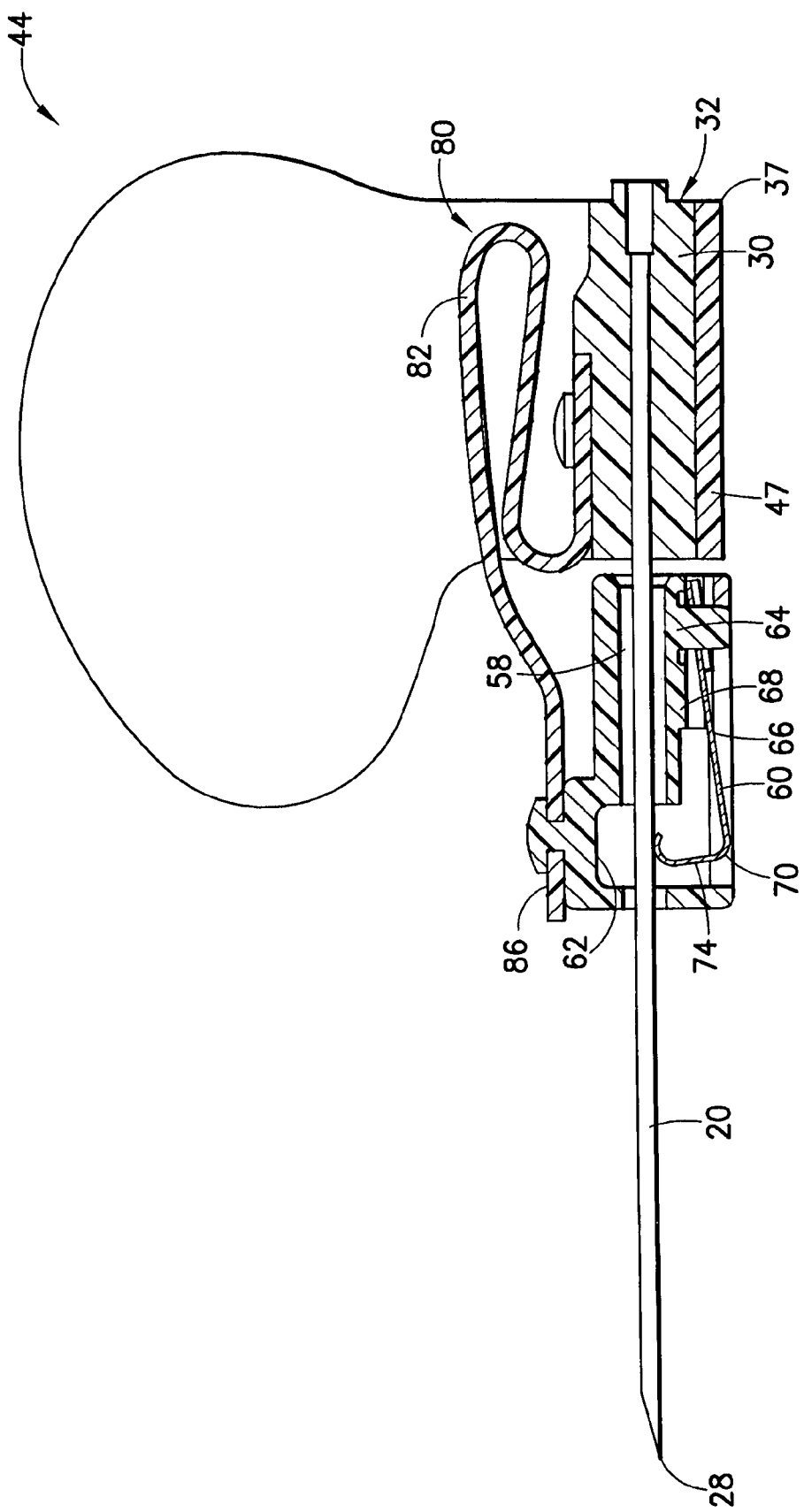
FIG. 5 is a side cross-sectional view of the shieldable needle device of FIG. 4.
Figure 6:
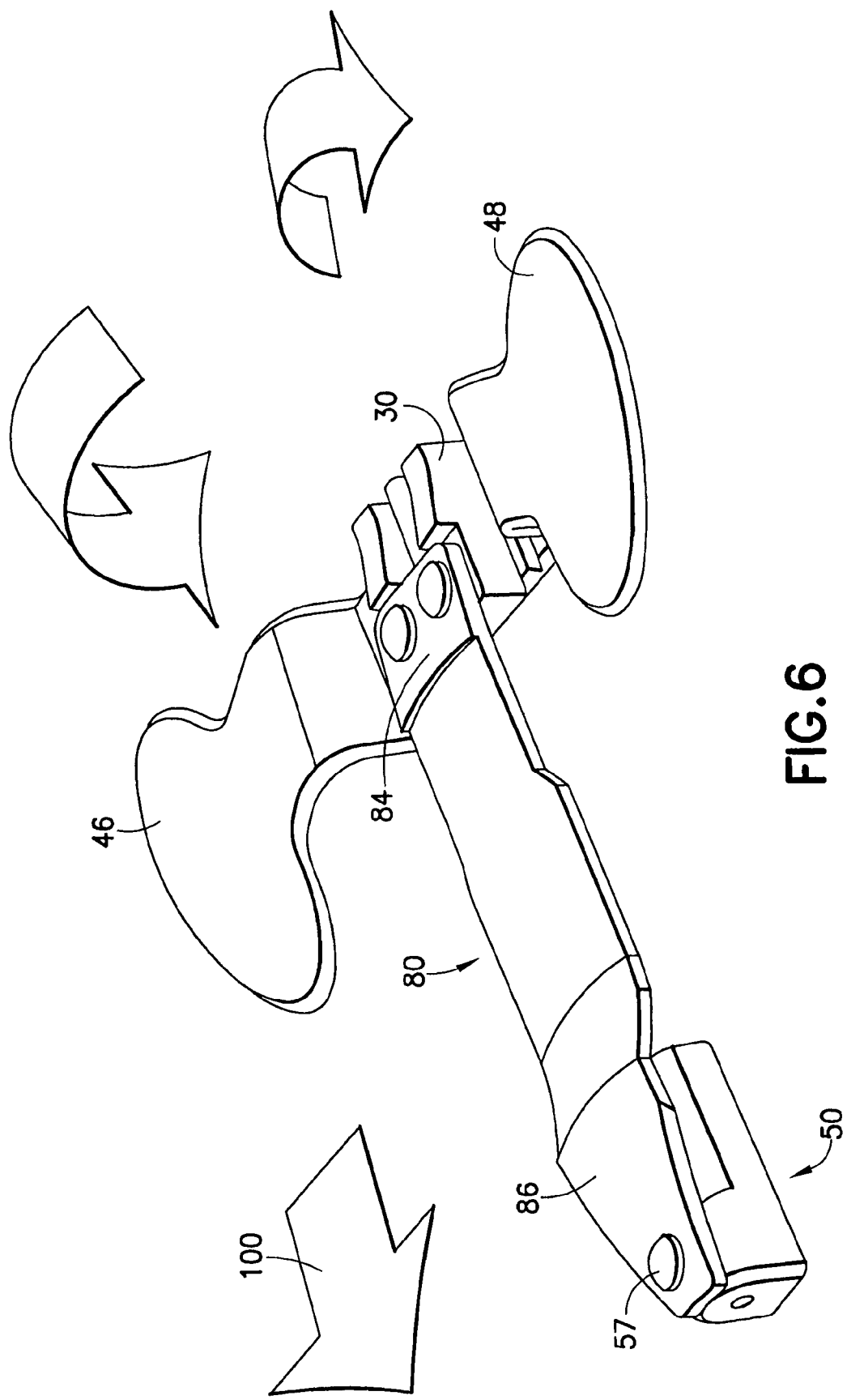
FIG. 6 is a perspective view of the shieldable needle device in an extended shielding position.
Figure 7:
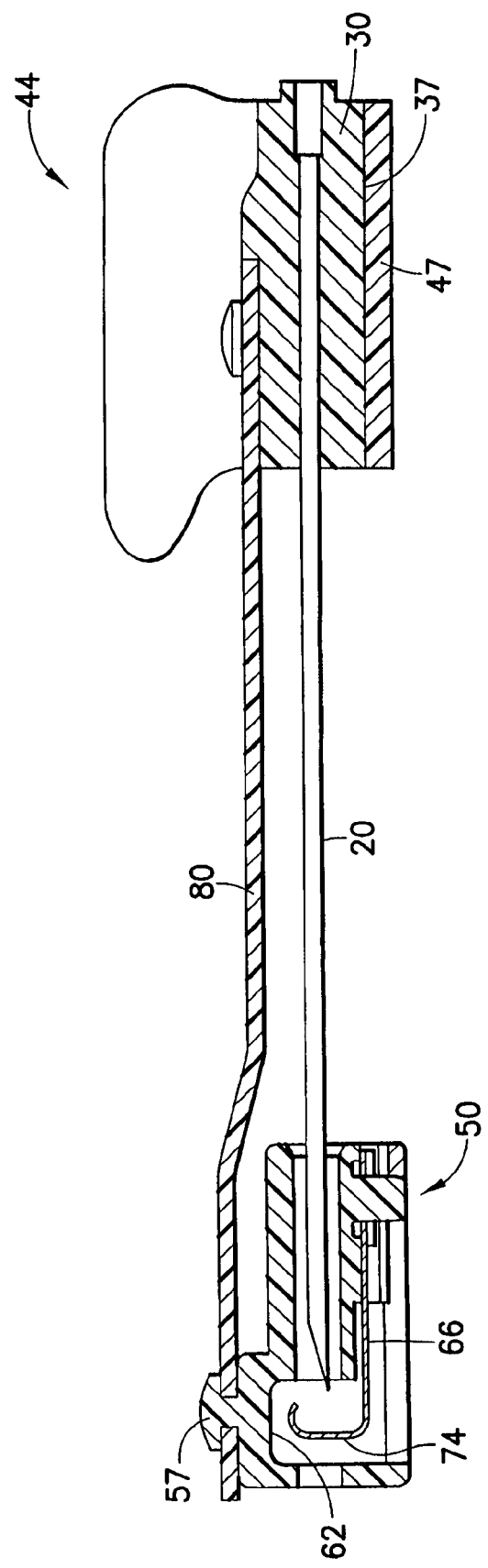
FIG. 7 is a side cross-sectional view of the shieldable needle device of FIG. 6 in the extended shielding position.

Needle assembly 12 further includes tip guard assembly 50, which extends co-axially about needle cannula 20 and is movable along needle cannula 20 between a first proximal position adjacent hub 30, and a second distal position adjacent puncture tip 28, as will be described in more detail herein. Tip guard assembly 50 desirably includes a housing 52 and a protective clip 60. Housing 52 is a unitary structure, desirably molded from a thermoplastic material, including a recessed slot area 53, a proximal end 54, a distal end 56, and an internal passage 58 extending between the ends. Portions of internal passage 58 adjacent distal end 56 define an enlarged clip receptacle 62, as shown in FIGS. 5 and 7. Additionally, tip guard assembly 50 includes an extending button member 57 which extends from the top portion of housing 52, desirably at the distal end thereof. A clip mounting post 64 extends downwardly from housing 52 at a location near proximal end 54 of housing 52.

Clip 60 is unitarily stamped and formed from a resiliently deflectable metallic material. Clip 60 includes a planar spring leg 66 with a proximal end 68 and an opposed distal end 70. A mounting aperture 72 extends through spring leg 66 at a location near proximal end 68. Mounting aperture 72 has a diameter approximately equal to or slightly less than the diameter of mounting post 64 of housing 52. As such, mounting post 64 can be forced through mounting aperture 72 when the axis of mounting post 64 and the axis of mounting aperture 72 are substantially collinear. A lock out leg 74 extends from distal end 70 of spring leg 66. The extending lock out leg 74 enables secure protective engagement with puncture tip 28 of needle cannula 20 and further enables smooth axial sliding movement of tip guard assembly 50 along needle cannula 20, as explained further herein.

Hub 30 and tip guard assembly 50 are interconnected through drive member 80. Drive member 80 provides for axial movement of tip guard assembly 50 along needle cannula 20 from a first proximal position adjacent hub 30 to a second distal position adjacent puncture tip 28, as will be described in more detail herein.

Drive member 80 includes a body 82 having a proximal end 84 and a distal end 86. Body 82 is desirably a resilient flexible material capable of bending and/or extending without an application of force, such as silicone. For example, prior to use, the drive member 80 is in a folded biased position, and upon release of the wings 46 and 48, as will be described hereinafter, the drive member 80 extends forward. Proximal end 84 of body 82 of drive member 80 includes structure for mating with hub 30, such as two circular openings 88 for receiving the button elements 35 on distal end 34 of hub 30, thereby securing the proximal end 84 of the drive member 80 to the distal end 34 of hub 30. Distal end 86 of body 82 of drive member 80 includes a circular opening 92 to mate with the extending button member 57 on distal end 56 of the tip guard assembly 50. Alternatively or in addition to the mechanical mating structure provided by button elements 35 and openings 88, proximal end 84, as well as distal end 86 of body 82 may be fixedly attached to tip guard assembly 50, such as through the use of an adhesive or the like.

Since proximal end 84 of body 82 is connected to distal end 34 of hub 30, and since the wings 46 and 48 extend laterally from hub 30, movement of the wings 46 and 48 results in the corresponding movement of drive member 80. In particular, when in a dorsal position, the wings 46 and 48 retain the drive member 80 in a folded biased position. Additionally, wings 46 and 48 in a dorsal position create a gap 94 between the hub 30 and wings 46 and 48 thereby retaining a portion of drive member 80 internally within gap 94. This acts to maintain the tip guard assembly 50 in a proximal position adjacent the distal end 34 of hub 30. Upon release of wings 46 and 48, wings 46 and 48 are free to move automatically from the dorsal position in which they are bent together to form a unitary dorsal structure to the relaxed, laterally extending position in turn, eliminating gap 94. As such, the body 82 of drive member 80 is no longer retained by wings 46 and 48, and unfolds to extend the tip guard assembly 50 in a direction toward distal end 24 of needle cannula 20. Moreover, since distal end 86 of body 82 is fixedly attached to tip guard assembly 50, and since tip guard assembly 50 is actually movable along needle cannula 20, the release of wings 46 and 48 causes tip guard assembly 50 to axially move in the direction of arrow 100, away from hub 30 and toward distal end 24 of needle cannula 20, where tip guard assembly 50 can effectively shield puncture tip 28.

Tip guard assembly 50 moves axially along needle cannula 20 toward distal end 24 during movement of drive member 80 through corresponding movement between wings 46 and 48 and body 82. Release of wings 46 and 48 from the dorsal position to a laterally extending position causes body 82 of drive member 80 to unfold and extend toward distal end 24 of needle cannula 20. Body 82 is a flexible material biased toward the extending position, and therefore acts as a means for storing energy to extend body 82 toward distal end 24 of needle cannula 20 upon corresponding movement between wings 46 and 48, thereby propelling tip guard assembly 50 from the proximal position to the distal position.

Assembly of blood collection set 10 may be accomplished as follows. Tip guard assembly 50 is assembled by forcing mounting post 64 of tip guard housing 52 through mounting aperture 72 of clip 60. Spring leg 66 of clip 60 is then urged downwardly or away from internal passage 58 through tip guard housing 52. Drive member 80 is then interconnected between tip guard assembly 50 and hub 30 by depressing openings 88 and 92 over buttons 35 and 57, respectively. Distal end 22 of needle cannula 20 is then passed through internal passage 38 of hub 30, and urged into internal passage 58 at proximal end 54 of tip guard housing 52. The downward deflection of spring leg 66 enables distal end 24 of needle cannula 20 to be passed entirely through tip guard housing 52. Spring leg 66 can be released after puncture tip 28 of needle cannula 20 passes entirely through tip guard housing 52. Thus, the end of lock out leg 74 will be biased against and slide along needle cannula 20. Tip guard assembly 50 then is slid proximally along needle cannula 20 into a position adjacent hub 30, with drive member 80 folded over itself into a bent, biased position, primed for use. Wings 46 and 48 are then bent toward each other in a dorsal manner to form a dorsally mating structure. Packaging cover 18 is then urged over puncture tip 28 and urged proximally over needle cannula 20, with puncture tip 28 safely maintained and disposed within packaging cover 18, and with the lateral side 17 and notch or slot 19 of packaging shield 18 maintaining wings 46 and 48 in the bent dorsal position. Packaging cover 18 is desirably constructed of a rigid material which is capable of maintaining wings 46, 48 in the dorsal position.

Blood collection set 10 can be packaged substantially in the condition shown in FIG. 1, such as in a blister package. Prior to use, blood collection set 10 is removed from its package, and fixture 16 may be connected to an appropriate receptacle for providing fluid communication with lumen 28 through needle cannula 20.

In use, blood collection set 10 is provided with needle device 12 assembled and including flexible tube 14 extending from needle device 12 and connected to fixture 16. After removing blood collection set 10 from its package, it can be assembled with other appropriate medical equipment for use. For example, a non-patient needle assembly and a needle holder may be connected to blood collection set 10 through fixture 16.

Figure 3:
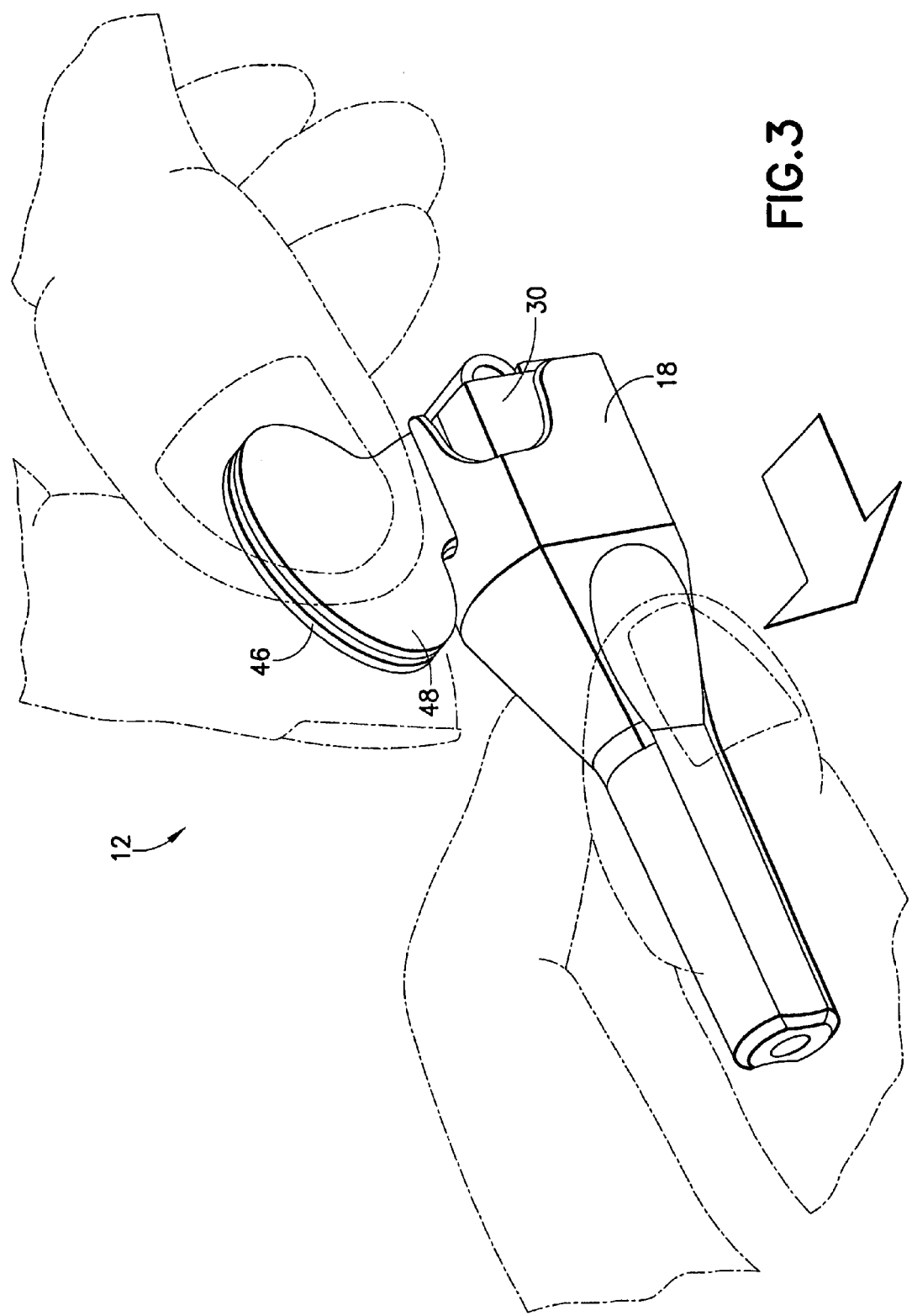
FIG. 3 is a perspective view of the shieldable needle device of FIG. 1 in use.

To prepare for use of blood collection set 10, the user grasps blood collection set 10 at needle device 12, placing a thumb and forefinger between wings 46 and 48 of hub 30, with wings 46 and 48 maintained in a dorsal position between the user's fingers, as shown in FIG. 3. Both wings 46 and 48 are preferably flexed or bent toward each other between a user's thumb and forefinger with body 82 of drive member 80 trapped therebetween. Packaging cover 18 is then grasped and urged distally to disengage from needle cannula 20, thereby exposing puncture tip 28 of needle cannula 20.

The medical practitioner can then urge puncture tip 28 at distal end 24 of needle cannula 20 into a targeted blood vessel of a patient, while wings 46 and 48 are maintained between thumb and forefinger to assist in controlled entry by the medical practitioner. Tip guard assembly 50 is maintained in the proximal position due to the grip by the user's fingers between wings 46 and 48, which maintains drive member 80 in the folded, biased state.

After the targeted blood vessel has been accessed, the medical practitioner can release wings 46 and 48. Once the user releases the device, drive member 80 is free to move from the folded bias position to the extending unfolded position, due to the bias exerted by body 82 of drive member 80 through release of wings 46 and 48. Such movement causes body 82 to extend, thereby propelling tip guard assembly 50 distally along needle cannula 20 in an axial direction of arrow 100, with tip guard assembly 50 sliding or gliding along needle cannula 20 toward distal end 24. Distal movement of tip guard assembly 50 will terminate when proximal end 54 of tip guard housing 52 contacts the skin of the patient near the puncture site.

Upon completion of the procedure, such as when all desired samples have been drawn, needle cannula 20 is withdrawn from the patient. This removal of needle cannula 20 from the patient will permit further extension of body 82 and a corresponding distal movement of tip guard assembly 50 in an axial direction of arrow 100. After tip guard assembly 50 is moved along needle cannula 20 to the distal end 24, lockout leg 74 of clip 60 will pass distally beyond puncture tip 28 of needle cannula 20. The inherent resiliency of spring leg 66 of clip 60 will urge lockout leg 74 over puncture tip 28 of needle cannula 20. Thus, a return movement of tip guard assembly 50 is prevented. Furthermore, drive member 80 has an overall dimension that will prevent movement of tip guard assembly 50 distally beyond needle cannula 20. Hence, puncture tip 28 of needle cannula 20 is safely shielded. Blood collection set 10 may then be appropriately discarded.

Since wings 46 and 48 are initially bent in a dorsal position, wings 46 and 48 can act as a handle portion during insertion, withdrawal and disposal of needle device 12. In particular, after release of wings 46 and 48 to propel tip guard assembly 50 to the distal position shielding needle cannula 20, wings 46 and 48 extend laterally from hub 30. Since wings 46 and 48 are a flexible rigid structure, wings 46 and 48 can be bent to a dorsal position to grip needle device 12 after removal from the patient, and can act as a handle portion for carrying blood collection set 10 at a position remote from the used needle tip of cannula 20. Additionally, drive member 80 can be activated while puncture tip 28 is within the patient's blood vessel, thereby axially moving tip guard assembly 50, axially along needle cannula 20, or may be activated after puncture tip 28 is removed from the patient's blood vessel.

The shielding feature of the present invention is passively activated upon normal usage of the device. In particular, upon removal of the packaging cover prior to insertion, the safety feature is primed and charged, ready for shielding the needle once the user releases the wing structure after insertion into a patient. Moreover, as described above, passive shielding of the needle cannula is automatically achieved merely by removing needle cannula from the patient.

In some instances, the needle device may be dropped or knocked from the hand of the medical practitioner either before venipuncture or during a medical procedure. The passive shielding described above will commence automatically when the needle device is dropped or knocked from the medical practitioner's hand. Thus, the automatic shielding may be triggered by the intentional or unintentional release of the wings by the medical practitioner.

Moreover, a medical practitioner does not always enter the targeted blood vessel during the first venipuncture attempt. However, a medical practitioner typically retains a close grip on the needle device until the targeted blood vessel has been entered. In this instance, the continued gripping of the wings will prevent the needle from shielding until the targeted blood vessel has been punctured. The second attempt at accessing a targeted blood vessel generally is a very low risk procedure in which the practitioner's hand is spaced considerably from the puncture tip of the needle cannula. Thus, the blood collection set according to the present invention does not involve the inconvenience of having to use a new blood collection set following each unsuccessful venipuncture attempt.

While the needle assembly of the present invention has been described in terms of one embodiment for use in connection with a blood collection system, it is further contemplated that the needle assembly could be used with other medical procedures, such as in conjunction with a conventional intravenous infusion set, which are well known in the art for use with needle assemblies.

While the present invention is satisfied by embodiments in many different forms, there is shown in the drawings and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed:

1. A shieldable needle device comprising:
a needle cannula having proximal and distal ends;
a hub supporting said proximal end of said needle cannula;
a pair of wings extending laterally from opposing sides of the hub, said wings being bendable between a laterally extending position and a dorsal position;
a tip guard axially movable along said needle cannula from a proximal position substantially adjacent said hub to a distal position where said tip guard protectively surrounds said distal end of said needle cannula;
a drive member extendable between a folded biased position and an extended position for moving said tip guard from said proximal position to said distal position, said drive member comprising a first end connected to said hub and a second end connected to said tip guard, said pair of wings retaining said drive member in said folded biased position when in said dorsal position, thereby maintaining the tip guard in the proximal position, with release of said wings from said dorsal position to said laterally extending position allowing said drive member to unfold and extend the tip guard from the proximal position toward the distal position; and
a removable packaging cover protectively surrounding said needle cannula and maintaining said wings in said dorsal position.

2. The device as in claim 1, wherein the packaging cover includes a slot area for receiving and maintaining said wings in said dorsal position.

3. The device as in claim 1, wherein said wings are integrally formed with said hub.

4. The device as in claim 1, wherein said wings are formed of a resilient flexible material.

5. The device as in claim 1, wherein said drive member is formed of a resilient flexible member.

6. The device as in claim 1, wherein said tip guard comprises a tip guard housing formed from a plastic material and a metallic spring clip being mounted to said housing, said spring clip being biased against said needle cannula when said tip guard is in said proximal position and being resiliently moved over said distal end of said needle cannula when said tip guard is in said distal position.

7. The device as in claim 1, wherein said proximal end of said hub is adapted for mating with a medical device.

8. The device as in claim 1, wherein said device further comprises a flexible tube extending from said proximal end of said hub, said flexible tube including structure for mating with a blood collection assembly.

9. A shieldable needle device comprising:
a needle cannula having proximal and distal ends;
a hub supporting said proximal end of said needle cannula;
a pair of wing surfaces extending laterally from opposing sides of the hub, said wings being bendable between a laterally extending position and a dorsal position whereby a gap is created between said hub and said wing surfaces when in said dorsal position;
a tip guard axially movable along said needle cannula from a proximal position to a distal position where said tip guard protectively surrounds said distal end of said needle cannula;
a drive member extendable between a folded biased position and an extended position for moving said tip guard from said proximal position to said distal position, said drive member comprising a first end connected to said hub and a second end connected to said tip guard, wherein a portion of said drive member in said folded biased position is retained internal to said gap while said wing surfaces are in dorsal position and
a removable packaging cover having an opening for protectively surrounding said needle cannula, wherein the packaging cover includes structure for removably mating with said device and includes a slot area for maintaining said wings in said dorsal position.

10. The device as in claim 9, wherein said wing surfaces in said dorsal position maintain the tip guard in the proximal position and release of said wing surfaces from said dorsal position to said laterally extending position allows said drive member to unfold and extend the tip guard from the proximal position toward the distal position.

11. The device as in claim 9, wherein said wing surfaces are integrally formed with said hub.

12. The device as in claim 9, wherein said wing surfaces comprise a unitary member are formed of a resilient flexible material.

13. The device as in claim 9, wherein said drive member is formed of a resilient flexible member.

14. The needle device as in claim 9, wherein said tip guard comprises a tip guard housing formed from a plastic material and a metallic spring clip being mourned to said housing, said spring clip being biased against said needle cannula when said tip guard is in said proximal position and being resiliently moved over said distal end of said needle cannula when said tip guard is in said distal position.

* * * * *